(12) United States Patent
Wu et al.

(10) Patent No.: US 11,337,614 B2
(45) Date of Patent: May 24, 2022

(54) MULTI-TARGET VITAL SIGN DETECTION SYSTEM AND METHOD

(71) Applicant: PEGATRON CORPORATION, Taipei (TW)

(72) Inventors: Chien-Yi Wu, Taipei (TW); Tse-Hsuan Wang, Taipei (TW); Po-Yuan Chen, Taipei (TW); Chao-Hsu Wu, Taipei (TW)

(73) Assignee: PEGATRON CORPORATION, Taipei (TW)

( * ) Notice: Subject to any disclaimer, the term of this patent is extended or adjusted under 35 U.S.C. 154(b) by 409 days.

(21) Appl. No.: 16/722,668

(22) Filed: Dec. 20, 2019

(65) Prior Publication Data

US 2020/0268257 A1 Aug. 27, 2020

(30) Foreign Application Priority Data

Feb. 27, 2019 (TW) ................. 108106659

(51) Int. Cl.
*A61B 5/0205* (2006.01)
*A61B 5/00* (2006.01)

(52) U.S. Cl.
CPC .......... *A61B 5/0205* (2013.01); *A61B 5/0015* (2013.01); *A61B 5/72* (2013.01)

(58) Field of Classification Search
CPC ....... A61B 5/0205; A61B 5/0015; A61B 5/72; A61B 5/0507; A61B 5/7235
See application file for complete search history.

(56) References Cited

U.S. PATENT DOCUMENTS

| 2015/0369911 | A1 | 12/2015 | Mabrouk et al. |
| 2018/0279884 | A1* | 10/2018 | Ahmad ................. A61B 5/725 |
| 2019/0216393 | A1* | 7/2019 | Baheti ...................... G01S 13/88 |
| 2020/0292688 | A1* | 9/2020 | Tseng ................... G01S 13/343 |
| 2020/0300972 | A1* | 9/2020 | Wang ................... A61B 5/0507 |

FOREIGN PATENT DOCUMENTS

CN 108577815 A 9/2018

* cited by examiner

*Primary Examiner* — John R Downey
(74) *Attorney, Agent, or Firm* — Li & Cai Intellectual Property (USA) Office (57) ABSTRACT

A multi-target vital sign detection system includes a transmitter, a receiver and a processor. The transmitter is configured to transmit a millimeter wave signal to a detection area, and the receiver is configured to receive a reflecting millimeter wave signal reflected by a plurality of targets in the detection area. The processor is configured to: generate signal strength versus distance data by analyzing the received reflecting millimeter wave signal; perform an extreme value reserving process to generate signal extreme value versus distance data; perform a peak search algorithm to obtain a peak list including a plurality of peak values and a plurality of corresponding peak distances; generate a distance array including a plurality of distance variables; and perform a vital sign detection algorithm to generate multiple sets of vital sign data.

20 Claims, 6 Drawing Sheets

| Target 1 | Target 2 |
| --- | --- |
| 27 | 81 |
| Breath 25.78 | Breath 11.72 |
| Heartbeat 59.77 | Heartbeat 69.14 |

| Target 3 | Target 4 |
| --- | --- |
| 61 | 0 |
| Breath 17.58 | Breath 0 |
| Heartbeat 50.39 | Heartbeat 0 |

Distance variable

MULTI-TARGET VITAL SIGN DETECTION SYSTEM AND METHOD

CROSS-REFERENCE TO RELATED PATENT APPLICATION

This application claims the benefit of priority to Taiwan Patent Application No. 108106659, filed on Feb. 27, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a vital sign detection system and method, and more particularly to a multi-target vital sign detection system and method.

BACKGROUND OF THE DISCLOSURE

In a conventional vital sign detecting device, the Doppler phase shift caused by a displacement of the body of a target organism can be directly eliminated by transmitting a single signal through two antennas to opposite sides of the target organism, thereby achieving vital sign detection. In this architecture, only one radar device is needed, and the vital sign detection can be performed with toleration for large displacement of the organism body without a high linearity requirement for the radar device.

However, the existing technology for detecting respiratory and heart rate using radar are merely designed for close-range detection of a single target organism. Under this architecture, it is impossible to simultaneously detect the return signals of multi-target organisms at different distances.

SUMMARY OF THE DISCLOSURE

In response to the above-referenced technical inadequacies, the present disclosure provides a multi-target vital sign detection system and method.

In one aspect, the present disclosure provides a multi-target vital sign detection system including a transmitter, a receiver and a processor. The transmitter is configured to transmit a millimeter wave signal to a detection area, and the receiver is configured to receive a reflecting millimeter wave signal reflected by a plurality of targets in the detection area. The processor is coupled to the transmitter and the receiver and configured to: generate multiple sets of signal strength versus distance data according to the received reflecting millimeter wave signal; perform an extreme value reserving process on the multiple sets of signal strength versus distance data to generate at least one set of signal extreme value versus distance data; perform a peak search algorithm on the at least one set of signal extreme value versus distance data to generate a peak list, in which the peak list includes a plurality of peak values, and each of the plurality of peak values corresponds to one of a plurality of peak distances; generate a distance array according to a number of targets to be detected and the plurality of peak distances, wherein the distance array includes a plurality of distance variables, and a number of the distance variables corresponds to the number of targets to be detected; and perform a vital sign detection algorithm on the peak values corresponding to the distance variables to generate multiple sets of vital sign data of the plurality of targets.

In one aspect, the present disclosure provides a multi-target vital sign detection method including: configuring a transmitter to transmit a millimeter wave signal to a detection area; configuring a receiver to receive a reflecting millimeter wave signal reflected by a plurality of targets in the detection area; and configuring a processor to: continuously analyze the received reflecting millimeter wave signal to generate multiple sets of signal strength versus distance data; perform an extreme value reserving process on the multiple sets of signal strength versus distance data to generate at least one set of signal extreme value versus distance data; perform a peak search algorithm on the at least one set of signal extreme value versus distance data to generate a peak list, in which the peak list includes a plurality of peak values, and each of the plurality of peak values corresponds to one of a plurality of peak distances; generate a distance array according to a number of targets to be detected and the plurality of peak distances, wherein the distance array includes a plurality of distance variables, and a number of the distance variables corresponds to the number of targets to be detected; and perform a vital sign detection algorithm on the peak values corresponding to the distance variables to generate multiple sets of vital sign data of the plurality of targets.

Therefore, detecting the return signals from different distances of several individuals at once by the aforementioned system and method of the present disclosure to observe and calculate the respiratory and heart rate of multiple target human bodies can be achieved.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 1:
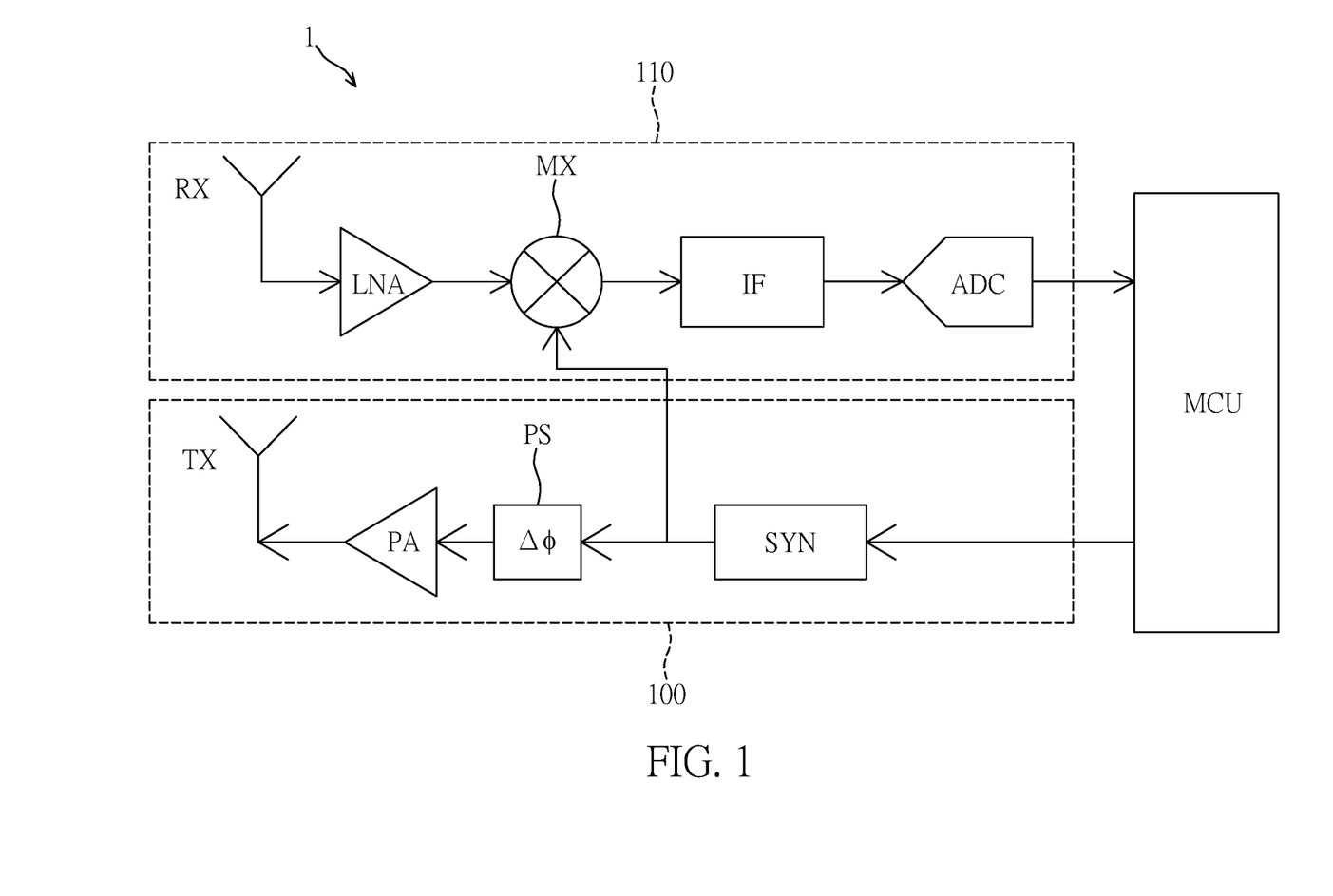
FIG. 1 is a system architecture diagram of a multi-target vital sign detection system according to an embodiment of the present disclosure.

Reference is made to FIG. 1, which is a system architecture diagram of a multi-target vital sign detection system according to an embodiment of the present disclosure. As shown in FIG. 1, an embodiment of the present disclosure provides a multi-target vital sign detection system 1 including a transmitter 100, a receiver 110, and a microprocessor MCU. The transmitter 100 is configured to transmit a millimeter wave signal to the detection area, and the receiver 110 is configured to receive the reflecting millimeter wave signal reflected by the plurality of targets in the detection area. Millimeter waves (mm Wave) are a special type of radar technology that uses short-wavelength electromagnetic waves. The electromagnetic wave signals emitted from a radar system are blocked by objects on a transmission path and then reflected. The complete millimeter wave radar system includes transmitting (TX) and receiving (RX) radio frequency (RF) components, analog components such as clock circuits, and digital components such as analog-to-digital converters (ADCs), microcontrollers (MCUs), and digital signal processors (DSPs).

Preferably, the transmitting antenna TX and the receiving antenna RX can be selected with a 77 GHz long distance millimeter wave radar antenna. Since the higher the frequency used by the radar, the shorter the wavelength, and the less the radar affected by the interference of light or the external environment, the resolution and accuracy will be higher. On the other hand, because the millimeter wave radar has a high operating frequency, it is suitable for detecting small distance variations, that is, the vital sign detection can be performed by detecting phase changes of reflected waves.

Furthermore, a Frequency Modulated Continuous Waveform (FMCW) signal is used as the millimeter wave signal in the present disclosure. The fundamental concept in radar systems is the transmission of an electromagnetic signal that objects reflect in its path. In the signal used in FMCW radars, the frequency increases linearly with time, and this type of signal is also called a chirp. In the present embodiment, a hardware system of the millimeter wave radar can use a common FMCW architecture. As shown in FIG. 1, the transmitter 100 includes a transmitter antenna TX, a power amplifier PA, a phase shifter PS, and a synthesizer SYN. The receiver 110 includes a receiving antenna RX, a low noise amplifier LNA, a mixer MX, an intermediate frequency circuit IF, and an analog digital converter ADC.

The synthesizer SYN is used to generate a chirp, which is transmitted by the transmitting antenna TX. At this time, if an object is present in the detection area, the reflection of the chirp by the object generates a reflected chirp captured by the receiving antenna RX, which is the reflecting millimeter wave signal mentioned above. Next, the mixer MX is used to combine the signal of the transmitting antenna TX and the receiving antenna RX, and the mixer MX calculates a frequency difference between the transmitted wave and the received wave, and then down-converts and outputs intermediate frequency (IF) signals. An information of the detection target is further obtained through the IF circuit IF at a back end, and the signal is finally sent to the digital signal processor through the analog digital converter ADC for processing in the microprocessor MCU as shown.

The low noise amplifier LNA is electrically connected to the receiving antenna RX for making the reflected millimeter wave signal have greater gain and sensitivity, and the reflected millimeter wave signal having the greater gain is transmitted to the mixer MX.

In general, for adults, chest displacement due to breathing can be several millimeters. The displacement due to the heartbeat can be about several hundred microns. In order to measure these small displacements, it can use a phase of the FMCW signal at a distance of the target, and track the phase for a period of time.

Figure 2:
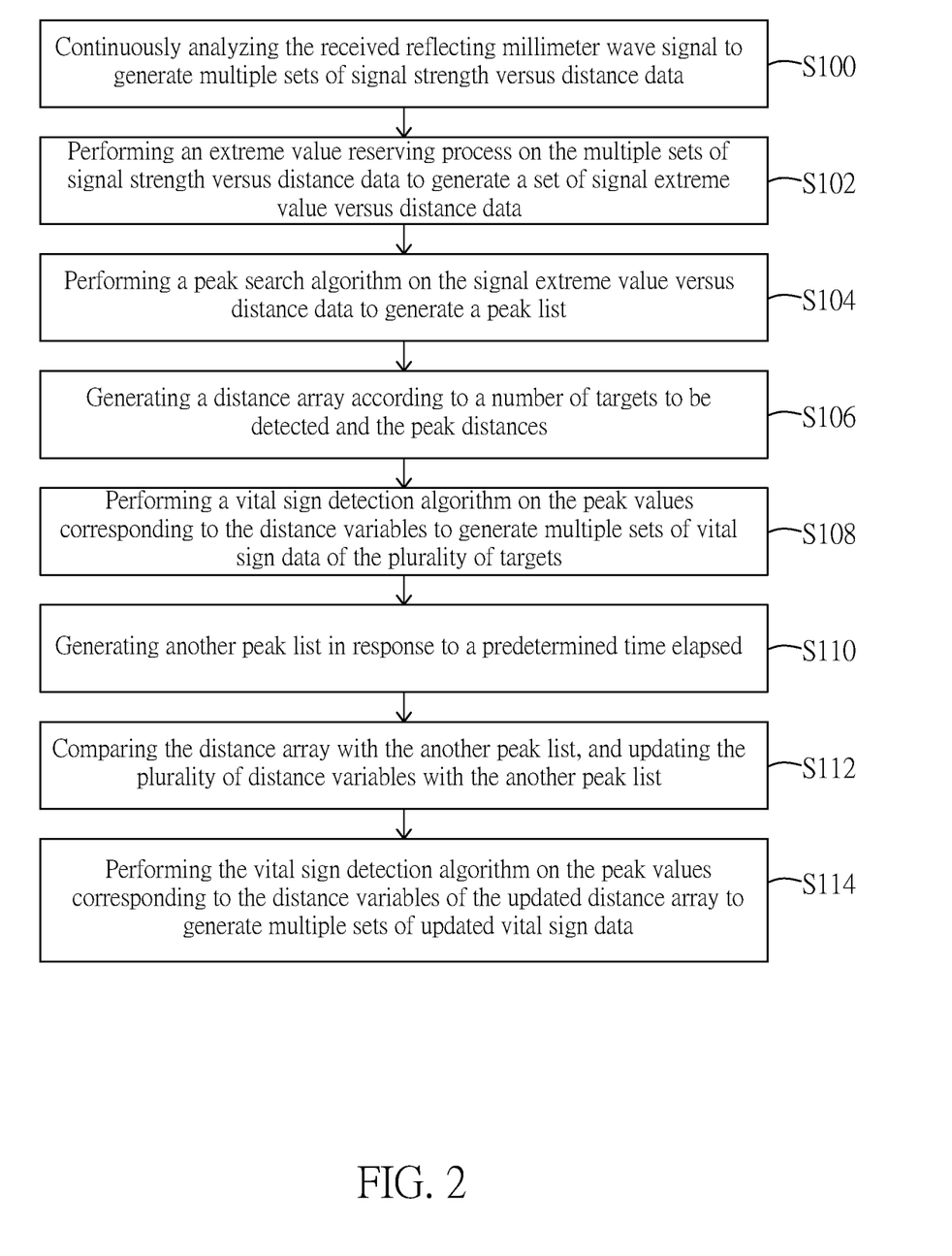
FIG. 2 is a flow chart of a detection algorithm according to an embodiment of the present disclosure.

Reference is made to FIG. 2, which is a flow chart of a detection algorithm according to an embodiment of the present disclosure. The processor coupled to the transmitter 100 and the receiver 110, such as the microcontroller MCU or a digital signal processor (DSP), is configured to perform the following steps:

Step S100: Continuously analyzing the received reflecting millimeter wave signal to generate multiple sets of signal strength versus distance data.

It should be noted that the present disclosure is capable of detecting return signals of a plurality of individuals at different distances simultaneously by utilizing the detection algorithm to process and detect the return signals at specific distances, and then analyze small changes in the phase, thereby observing and calculating numbers of breaths and heartbeats. Therefore, frequency modulated continuous waveform (FMCW) emitted by the radar is utilized to detect vibration changes of multiple target objects. For example, small vibrations caused by breathing and heartbeat, which can be processed by the detection algorithm to simultaneously monitor multiple targets and separately determine relevant parameters of the small phase changes, and the numbers of heartbeats and breaths of the multiple target objects can be obtained.

Step S102: Performing an extreme value reserving process on the multiple sets of signal strength versus distance data to generate at least one set of signal extreme value versus distance data.

In detail, a moving window can be set to generate the newly obtained signal strength versus distance data, and the at least one set of signal extreme value versus distance data can be obtained by performing the extreme value reserving process on the multiple sets of signal strength versus distance data generated by the moving window.

Figure 3:
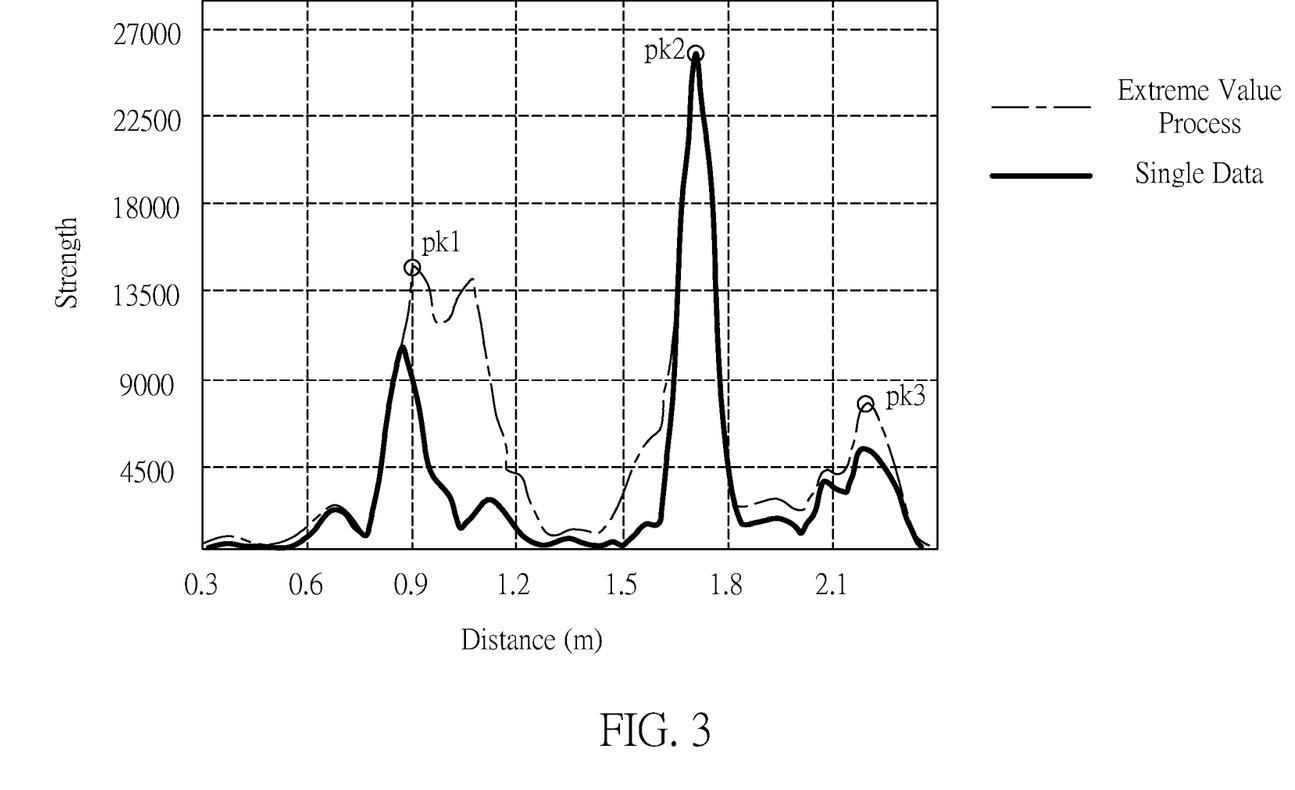
FIG. 3 is a schematic diagram of signal extreme value versus distance data and peaks generated by a moving window, an extreme value reserving process, and a peak search algorithm according to an embodiment of the present disclosure.

Reference is made to FIG. 3, which is a schematic diagram of signal extreme value versus distance data and peaks generated by a moving window, an extreme value reserving process, and a peak search algorithm according to an embodiment of the present disclosure. As shown in the figure, a solid line represents a single signal strength versus distance data generated after the analysis, and a broken line is the signal extreme value versus distance data obtained by the extreme value reserving process after the moving window generates a plurality of signal strength versus distance data. In the present embodiment, FIG. 3 shows the FMCW signal when the targets are three individuals observed through the detection system. The solid line in a frame of FIG. 3 is raw data of the FMCW signal, and the broken line is the signal detected after targets move slightly, processed by the moving window and the extreme value process and temporarily stored in the memory.

Step S104: Performing a peak search algorithm on the signal extreme value versus distance data to generate a peak list. The peak list includes a plurality of peak values, and each of the plurality of peak values corresponds to one of a plurality of peak distances. For example, the present embodiment searches three peaks pk1, pk2, and pk3 out, and their corresponding peak distances are 0.9, 1.7, and 2.2 meters, respectively. For example, the peak list can be named as peak list table in the vital sign detection algorithm, the peak list table stores the searched peaks and corresponding distances, which are collected in this table. It should be noted that the peaks in the peak list can be arranged according to the signal strengths.

Step S106: Generating a distance array according to a number of targets to be detected and the peak distances. In detail, the distance array includes a plurality of distance variables, and the user may set the number of targets to be detected to determine the number of the distance variables. For example, the distance array can be named as rangeBinIndex in the vital sign detection algorithm, and the target number of targets to be detected can be named as numVitalSigns. Therefore, an i-th element in the rangeBinIndex array can be rangeBinIndex[i], and i can be a value from 0 to numVitalSigns−1. For example, three peaks pk1, pk2, and pk3 are searched in FIG. 3, and three elements such as rangeBinIndex[0]=0.9, rangeBinIndex[1]=1.7, and rangeBinIndex[2]=2.2 can be generated, which indicates that detection results of the radar corresponds to different distances.

Step S108: Performing a vital sign detection algorithm on the peak values corresponding to the distance variables to generate multiple sets of vital sign data of the plurality of targets.

Figure 4:
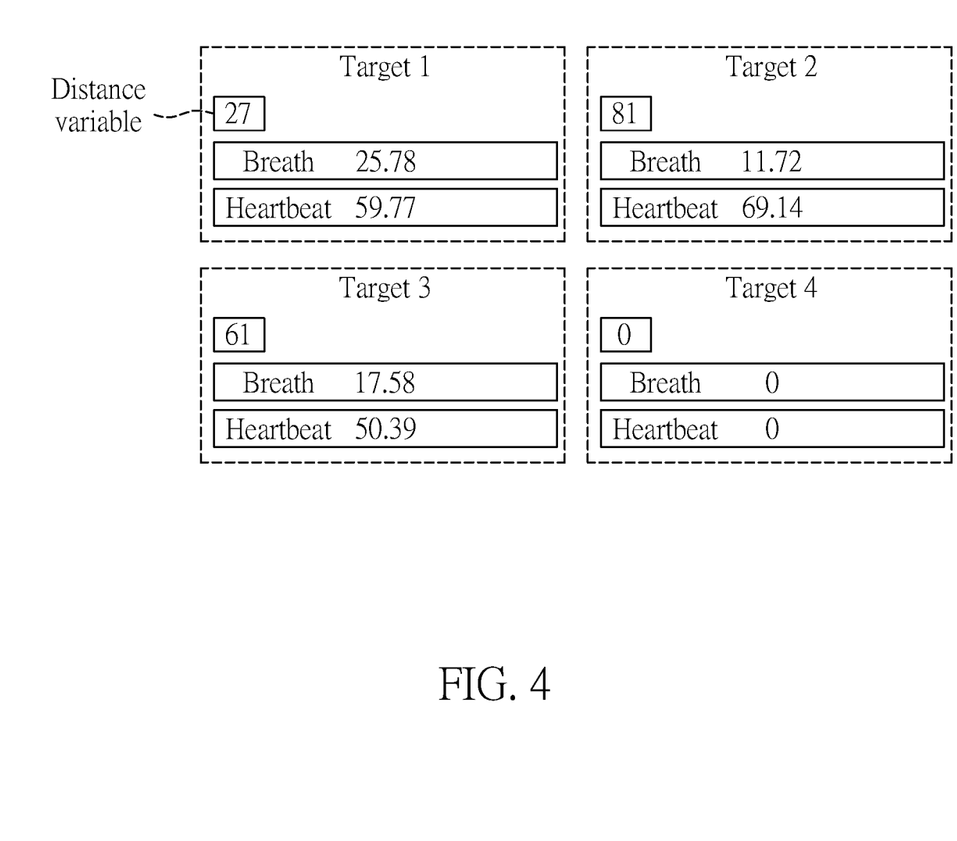
FIG. 4 is a schematic diagram of a numerical interface for detecting breathing and heartbeat through a vital sign algorithm according to an embodiment of the present disclosure.

Reference is made to FIG. 4, which is a schematic diagram of a numerical interface for detecting breath and heartbeat through a vital sign algorithm according to an embodiment of the present disclosure. As shown in FIG. 4, the present embodiment is an example in which the number of targets to be detected is set to 4, and the elements rangeBinIndex[i] of the targets 1 to 3 respectively correspond to the respective distance variables. In the present embodiment, the distance variable corresponding to the element rangeBinIndex[0] is 27, the distance variable corresponding to the element rangeBinIndex[1] is 81, and the distance variable corresponding to the element rangeBinIndex[2] is 61. Here, the distance variable is obtained by multiplying the peak distance by a constant k. The constant k is determined by actual condition of the hardware of the multi-target vital sign detecting system 1. When the number of targets to be detected is set to 4, and only 3 peaks are found, the distance variable corresponding to the element rangeBinIndex[3] is set to 0, indicating that the detection is stopped. Therefore, the vital sign detection algorithm only detects three distance variables to obtain vital signs such as breathing and heartbeat.

Step S110: Generating another peak list in response to a predetermined time elapsed. Here, the predetermined time is an update time set by the user to determine whether positions of the targets have changed. For example, the predetermined time may be 6 seconds, and a frequency of generating the signal strength versus the distance data may be set by a number of frames, for example, 20 frames per second. The aforementioned moving window can be set as the newly generated 10 frame signal strength versus distance data. In other words, the another peak list is generated by repeatedly performing the foregoing steps S100 to S104, and the distances of the targets can be locked by setting the update time while determining whether the target leaves the detection area.

Step S112: Comparing the distance array with the another peak list, and updating the plurality of distance variables with the another peak list.

Step S114: Performing the vital sign detection algorithm on the peak values corresponding to the distance variables of the updated distance array to generate multiple sets of updated vital sign data.

In the present embodiment, any object having a heartbeat or breathing, such as a person or an animal, can be detected by the vital sign detection algorithm. In addition, the reflected signal transmitted back through the FMCW can further obtain volumes of the targets and identify profiles of the targets.

In addition, when the multi-target vital sign detecting system 1 of the present disclosure is provided with a single transmitting antenna TX and a single receiving antenna RX, positions of the objects at different distances can be distinguished, but the present disclosure is not limited thereto. The multi-target vital sign detection system 1 can also include a plurality of transmitting antennas TX and a plurality of receiving antennas RX, which can utilize a direction of arrival (DOA) estimation technique to distinguish the targets at the same distance but in different directions. Then, the positions of the targets can be locked through the method of detecting multiple target objects in the present disclosure, and the vital characteristics of the breathing and heartbeat are analyzed.

The multi-target vital sign detection method of the present disclosure and another embodiment of comparing the distance array with another peak list will be described hereinafter.

Figure 5A:
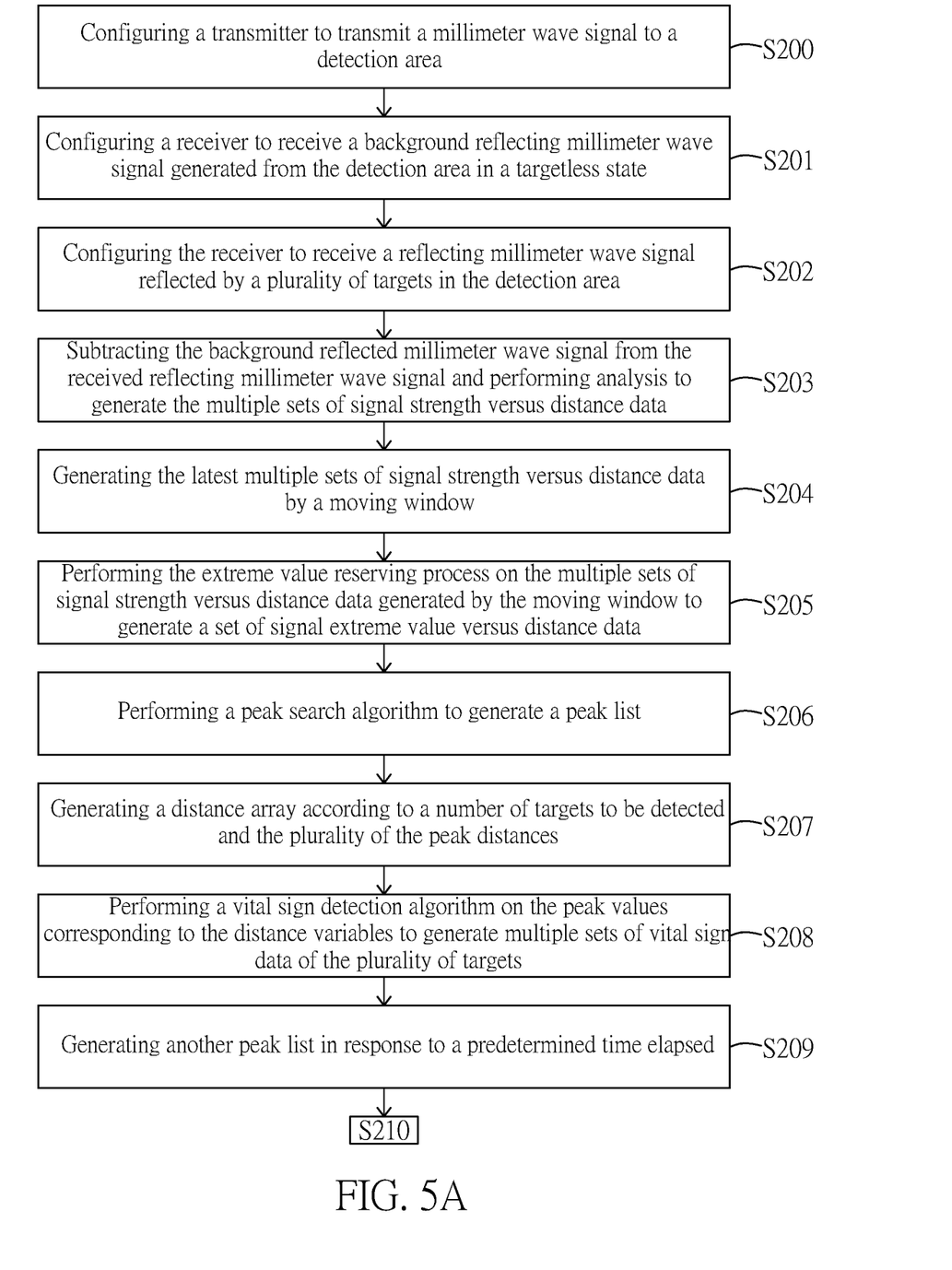
FIGS. 5A and 5B are flowcharts of a multi-target vital sign detection method according to another embodiment of the present disclosure.
Figure 5B:
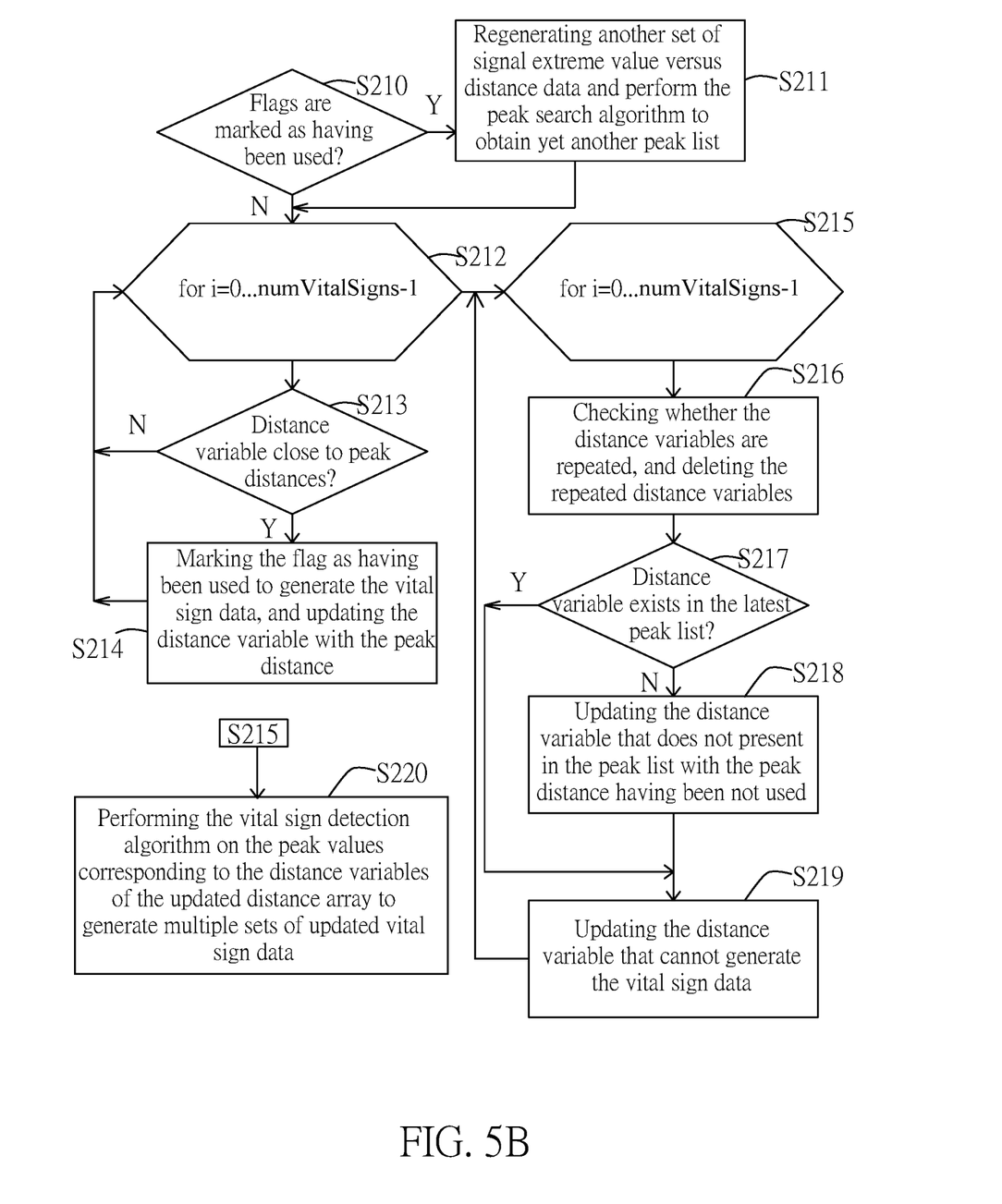

Reference is made to FIGS. 5A and 5B, which are flowcharts of a multi-target vital sign detection method according to another embodiment of the present disclosure. As shown in FIGS. 5A and 5B, another embodiment of the present disclosure provides a multi-target vital sign detection method, which is applicable to the multi-target vital sign detection system of the foregoing embodiments, and includes at least the following steps:

Step S200: Configuring a transmitter to transmit a millimeter wave signal to a detection area.

Step S201: Configuring a receiver to receive a background reflecting millimeter wave signal generated from the detection area in a targetless state. Specifically, before the vital sign detection is performed, the system can be corrected by means that the FMCW signal received in the targetless state is statistically averaged for several times and calculated as the reference value, which is corrected data.

Step S202: Configuring the receiver to receive a reflecting millimeter wave signal reflected by a plurality of targets in the detection area.

Further, the processor is configured to perform the following steps:

Step S203: Subtracting the background reflected millimeter wave signal from the received reflecting millimeter wave signal and performing analysis to generate the multiple sets of signal strength versus distance data.

Step S204: Generating the latest multiple sets of signal strength versus distance data by a moving window. In detail, after a reference value is subtracted from the received FMCW signal, the moving window and the extreme value reserving process are then utilized to prevent unstable issues from occurring, in which the unstable issues are caused by the unstable signal generated by a moving human body, resulting in difficulties in locking and detecting.

Step S205: Performing the extreme value reserving process on the multiple sets of signal strength versus distance data generated by the moving window to generate a set of signal extreme value versus distance data.

Step S206: Performing a peak search algorithm to generate a peak list.

It should be noted that the peaks in the peak list can be arranged according to the signal strengths, the peak list further includes a plurality of flags corresponding to the peak values, respectively. The plurality of flags are used to indicate whether the peak values have been used to generate the vital signs data. If the aforementioned vital signs data have been generated, that is, the peak values have been used to analyze vital signs, the peak values are marked as having been used. If the aforementioned vital signs have not been generated, that is, the peak values have not been used to analyze vital signs, the peak values are marked as having not been used. For example, vital signs can be generated starting from the peak value having the strongest signal strength.

Step S207: Generating a distance array according to a number of targets to be detected and the plurality of the peak distances.

Step S208: Performing a vital sign detection algorithm on the peak values corresponding to the distance variables to generate multiple sets of vital sign data of the plurality of targets.

Step S209: Generating another peak list in response to a predetermined time elapsed.

Step S210: checking whether flags of another peak list are marked as having been used. If yes, the method proceeds to step S211: Regenerating another set of signal extreme value versus distance data and perform the peak search algorithm to obtain yet another peak list, and the method proceeds to step S212; if not, the method proceeds directly to step S212.

Step S212: Successively checking each of the distance variables. As shown in FIG. 5B, a FOR loop is executed, and i-th distance variable of the distance array is checked, given that i is a value from 0 to numVitalSigns−1.

Step S213: Determining whether the distance variable is within a threshold range of one of the peak distances. In other words, it is determined whether the distance variable is close to one of the peak distances. In response to the distance variable being within the threshold range of one of the peak distances, the method proceeds to step S214. Step S214: making the flag as having been used to generate the vital sign data, and updating the distance variable with the peak distance. The method proceeds to step S212, assuming i=i+1, and checking the next distance variable. In response to the distance variable being not within the threshold range of one of the peak distances, the method returns to step S212, assuming i=i+1, and checking the next distance variable.

After all of the distance variables are checked, the method proceeds to step S215: successively checking each of the distance variables. As shown in FIG. 5B, another for loop is executed, and an i-th distance variable of the distance array is checked, given that i is a value from 0 to numVitalSigns−1, and the method proceeds to step S216.

Step S216: Checking whether the distance variables are repeated, and if the distance variables are repeated, deleting the repeated distance variables. For example, the distance variable is set to 0 as shown in FIG. 4.

Step S217: Determining whether the distance variable is present in the latest peak list. If yes, the method proceeds to step S219. If not, the method proceeds to step S218. Step S218: updating the distance variable that does not present in the peak list with the peak distance having been not used. That is, the distance variable that does not present in the peak list is updated to the peak distance corresponding to the flag marked as not having been used in the peak list, and the method proceeds to step S219. In other words, the target corresponding to the distance variable may move in the detection area, so that the vital sign detection can be performed on the position of the unused peak value having the second strongest signal strength.

Step S219: Updating the distance variable that cannot generate the vital sign data when the vital sign detection algorithm is executed with the peak distance corresponding to the flag marked as not having been used in the latest peak list. The method then returns to step S216, assuming i=i+1 and checking the next distance variable.

When all of the distance variables are checked, the method proceeds to step S220: Performing the vital sign detection algorithm on the peak values corresponding to the distance variables of the updated distance array to generate multiple sets of updated vital sign data.

In conclusion, the multi-target vital sign detection system and method provided by the present disclosure can detect multiple target objects having vital signs. In addition, volumes of the multiple target objects can be obtained from the reflected signal transmitted back through the FMCW, thereby identifying profiles of the multiple target objects.

Furthermore, after a reference value is subtracted from the received FMCW signal, the moving window and the extreme value reserving process are then utilized to prevent unstable issues from occurring, in which the unstable issues are caused by the unstable signal generated by a moving human body, resulting difficulties in locking and detecting. On the other hand, a plurality of transmitting antennas TX and a plurality of receiving antennas RX can be provided, which can utilize the direction of arrival (DOA) estimation technique to distinguish the targets at the same distance but in different directions. Then, the positions of the targets can be locked through the method of detecting multiple target objects in the present disclosure, and the vital characteristics of the breathing and heartbeat are analyzed.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A multi-target vital sign detection system comprising:
a transmitter configured to transmit a millimeter wave signal to a detection area;
a receiver configured to receive a reflecting millimeter wave signal reflected by a plurality of targets in the detection area; and
a processor coupled to the transmitter and the receiver, configured to:
generate multiple sets of signal strength versus distance data according to the received reflecting millimeter wave signal;
perform an extreme value reserving process on the multiple sets of signal strength versus distance data to generate at least one set of signal extreme value versus distance data;
perform a peak search algorithm on the at least one set of signal extreme value versus distance data to generate a peak list, wherein the peak list includes a plurality of peak values, and each of the plurality of peak values corresponds to one of a plurality of peak distances;
generate a distance array according to a number of targets to be detected and the plurality of peak distances, wherein the distance array includes a plurality of distance variables, and a number of the distance variables corresponds to the number of targets to be detected; and
perform a vital sign detection algorithm on the peak values corresponding to the distance variables to generate multiple sets of vital sign data of the plurality of targets.

2. The multi-target vital sign detection system according to claim 1, wherein the processor is further configured to:
generate the multiple sets of signal strength versus distance data by a moving window,
wherein the at least one set of signal extreme value versus distance data is obtained by performing the extreme value reserving process on the multiple sets of signal strength versus distance data generated by the moving window.

3. The multi-target vital sign detection system according to claim 1, wherein the receiver is further configured to receive a background reflecting millimeter wave signal generated from the detection area in a targetless state, and the processor is configured to subtract the background reflected millimeter wave signal from the received reflecting millimeter wave signal to generate the multiple sets of signal strength versus distance data.

4. The multi-target vital sign detection system according to claim 1, wherein the peak values in the peak list are arranged according to signal strengths.

5. The multi-target vital sign detection system according to claim 1, wherein in response to a predetermined time elapsed, the processor is further configured to:
generate another peak list;
compare the distance array with the another peak list, and update the plurality of distance variables with the another peak list; and
perform the vital sign detection algorithm on the peak values corresponding to the updated distance variables of the distance array to generate multiple sets of updated vital sign data.

6. The multi-target vital sign detection system according to claim 5, wherein the peak list further includes a plurality of flags corresponding to the peak values, respectively, and the plurality of flags are used to indicate whether the peak values have been used to generate the vital signs data,
wherein in a step that the processor is configured to compare the distance array with the another peak list and update the plurality of distance variables with the another peak list, the processor is further configured to:
check whether the flags of the peak list are marked as having been used to generate the multiple sets of vital sign data;
in response to the flags of the peak list being marked as having been used to generate the multiple sets of vital sign data, regenerate another set of signal extreme value versus distance data and perform the peak search algorithm to obtain yet another peak list; and
in response to the flags of the peak list being not marked as having been used to generate the multiple sets of vital sign data, successively check whether each of the plurality of distance variables is within a threshold range of one of the peak distances.

7. The multi-target vital sign detection system according to claim 6, wherein in response to the distance variable being within the threshold range of one of the peak distances, the processor is configured to mark the flag corresponding to the peak value of the distance variable within the threshold range as having been used to generate the vital sign data, and update the distance variable with the peak distance corresponding to the peak value.

8. The multi-target vital sign detection system according to claim 7, wherein after the processor is configured to successively check whether each of the distance variables is within the threshold range of one of the peak distances corresponding to the peak values, the processor is further configured to check whether each of the distance variables is present in the peak list, and if one of the distance variables is not present in the peak list, the processor is configured to update the one of the distance variables with the peak distance corresponding to the flag marked as not having been used to generate the vital sign data.

9. The multi-target vital sign detection system according to claim 8, wherein after the processor is configured to successively check whether each of the distance variables is within the threshold range of one of the peak distances corresponding to the peak values, the processor is further configured to update one of the distance variables that is not capable of obtaining the vital sign data when the vital sign detection algorithm is executed with the peak distance corresponding to the flag marked as not having been used to generate the vital sign data.

10. The multi-target vital sign detection system according to claim 9, wherein after the processor is configured to successively check whether each of the distance variables is within the threshold range of one of the peak distances corresponding to the peak values, the processor is further configured to check whether the distance variables are repeated, and if the distance variables are repeated, the processor is configured to delete the repeated distance variables.

11. A multi-target vital sign detection method includes:
configuring a transmitter to transmit a millimeter wave signal to a detection area;

configuring a receiver to receive a reflecting millimeter wave signal reflected by a plurality of targets in the detection area; and configuring a processor to:
continuously analyze the received reflecting millimeter wave signal to generate multiple sets of signal strength versus distance data;
perform an extreme value reserving process on the multiple sets of signal strength versus distance data to generate at least one set of signal extreme value versus distance data;
perform a peak search algorithm on the at least one set of signal extreme value versus distance data to generate a peak list, wherein the peak list includes a plurality of peak values, and each of the plurality of peak values corresponds to one of a plurality of peak distances;
generate a distance array according to a number of targets to be detected and the plurality of peak distances, wherein the distance array includes a plurality of distance variables, and a number of the distance variables corresponds to the number of targets to be detected; and
perform a vital sign detection algorithm on the peak values corresponding to the distance variables to generate multiple sets of vital sign data of the plurality of targets.

12. The multi-target vital sign detection method according to claim 11, wherein the processor is further configured to:
generate the latest multiple sets of signal strength versus distance data by a moving window,
wherein the at least one set of signal extreme value versus distance data is obtained by performing the extreme value reserving process on the multiple sets of signal strength versus distance data generated by the moving window.

13. The multi-target vital sign detection method according to claim 11, wherein the receiver is further configured to receive a background reflecting millimeter wave signal generated from the detection area in a targetless state, and the processor is configured to subtract the background reflected millimeter wave signal from the received reflecting millimeter wave signal to generate the multiple sets of signal strength versus distance data.

14. The multi-target vital sign detection method according to claim 11, wherein the peak values in the peak list are arranged according to signal strengths.

15. The multi-target vital sign detection method according to claim 11, wherein in response to a predetermined time elapsed, the processor is further configured to:
generate another peak list;
compare the distance array with the another peak list, and update the plurality of distance variables with the another peak list; and
perform the vital sign detection algorithm on the peak values corresponding to the distance variables of the updated distance array to generate multiple sets of updated vital sign data.

16. The multi-target vital sign detection method according to claim 15, wherein the peak list further includes a plurality of flags corresponding to the peak values, respectively, and the plurality of flags are used to indicate whether the peak values have been used to generate the vital signs data,
wherein in a step that the processor is configured to compare the distance array with the another peak list and update the plurality of distance variables with the another peak list, the processor is further configured to:
check whether the flags of the peak list are marked as having been used to generate the multiple sets of vital sign data;
in response to the flags of the peak list being marked as having been used to generate the multiple sets of vital sign data, regenerate another set of signal extreme value versus distance data and perform the peak search algorithm to obtain yet another peak list; and
in response to the flags of the peak list being not marked as having been used to generate the multiple sets of vital sign data, successively check whether each of the plurality of distance variables is within a threshold range of one of the peak distances.

17. The multi-target vital sign detection method according to claim 16, wherein in response to the distance variable being within the threshold range of one of the peak distances, the processor is configured to mark the flag corresponding to the peak value of the distance variable within the threshold range as having been used to generate the vital sign data, and update the distance variable with the peak distance corresponding to the peak value.

18. The multi-target vital sign detection method according to claim 17, wherein after the processor is configured to successively check whether each of the distance variables is within the threshold range of one of the peak distances corresponding to the peak values, the processor is further configured to check whether each of the distance variables is present in the peak list, and if one of the distance variables is not present in the peak list, the processor is configured to update the one of the distance variables with the peak distance corresponding to the flag marked as not having been used to generate the vital sign data.

19. The multi-target vital sign detection method according to claim 18, wherein after the processor is configured to successively check whether each of the distance variables is within the threshold range of one of the peak distances corresponding to the peak values, the processor is further configured to update one of the distance variables that cannot be used to obtain the vital sign data when the vital sign detection algorithm is executed with the peak distance corresponding to the flag marked as not having been used to generate the vital sign data.

20. The multi-target vital sign detection method according to claim 19, wherein after the processor is configured to successively check whether each of the distance variables is within the threshold range of one of the peak distances corresponding to the peak values, the processor is further configured to check whether the distance variables are repeated, and if the distance variables are repeated, the processor is configured to delete the repeated distance variables.

* * * * *